(12) United States Patent
Veneroni et al.

(10) Patent No.: US 9,072,835 B2
(45) Date of Patent: Jul. 7, 2015

(54) DEVICE FOR COLLECTING SAMPLES

(75) Inventors: Alain Veneroni, Spino d'Adda (IT); Mihai Diga, Friedrichsdorf (DE); Daniel Daetwyler, Pieterlen (CH); Dominik Uehlinger, Kerzers (CH)

(73) Assignee: PRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 551 days.

(21) Appl. No.: 13/322,993

(22) PCT Filed: May 27, 2010

(86) PCT No.: PCT/EP2010/057291
§ 371 (c)(1),
(2), (4) Date: Nov. 29, 2011

(87) PCT Pub. No.: WO2010/139590
PCT Pub. Date: Dec. 9, 2010

(65) Prior Publication Data
US 2012/0078168 A1   Mar. 29, 2012
US 2012/0253268 A2   Oct. 4, 2012

(30) Foreign Application Priority Data

Jun. 5, 2009   (EP) .................................... 09162022

(51) Int. Cl.
*A61M 1/28* (2006.01)
*A61M 1/16* (2006.01)

(52) U.S. Cl.
CPC ............... *A61M 1/28* (2013.01); *A61M 1/1619* (2014.02)

(58) Field of Classification Search
CPC ... A61M 1/28; A61M 2001/281; A61M 1/16; A61M 2205/12; A61M 2001/288; A61M 1/14; A61M 1/1696; A61M 1/3413
See application file for complete search history.

(56) References Cited

U.S. PATENT DOCUMENTS 6,228,047 B1 *   5/2001   Dadson ........................... 604/29
2009/0124963 A1   5/2009   Hogard et al.

FOREIGN PATENT DOCUMENTS

WO   WO 99/06082    2/1999
WO   WO 03/063929   8/2003

* cited by examiner

*Primary Examiner* — Aarti B Berdichevsky
(74) *Attorney, Agent, or Firm* — Jacobson Holman, PLLC.

(57) ABSTRACT

A device for collecting dialysate samples has an inlet for receiving a flow of dialysate, a plurality of outlets for providing a flow of saturated dialysate, and means for sequential selection of one of the outlets. The sequential selection means are actuated only by the flow of dialysate received from the inlet. A system for peritoneal dialysis includes the device for collecting dialysate samples.

18 Claims, 10 Drawing Sheets

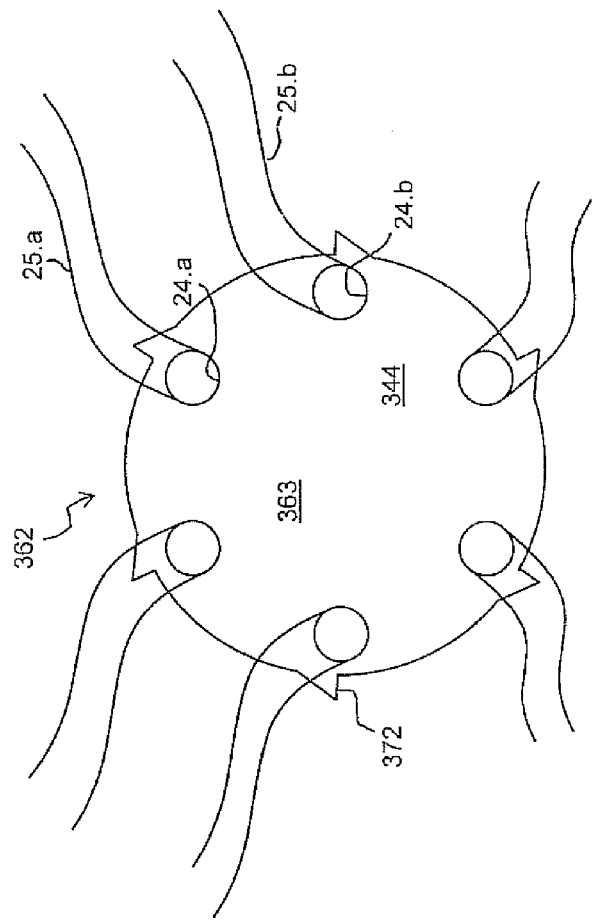
Fig. 10.b
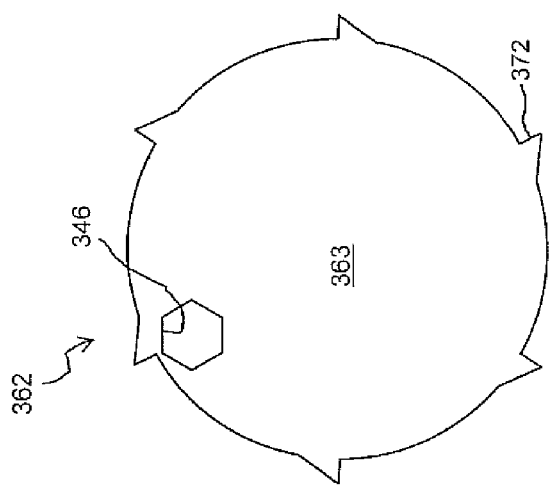
Fig. 10.a

DEVICE FOR COLLECTING SAMPLES

CROSS-REFERENCE TO RELATED APPLICATIONS

This is a national stage of PCT/EP10/057,291 filed May 27, 2010 and published in English, which claims the priority of European number 09162022.9 filed Jun. 5, 2009, hereby incorporated by reference.

BACKGROUND OF THE INVENTION

1. Field of Invention

The invention relates to a device for collecting fluid-samples in circuits, e.g. in circuits for peritoneal dialysis (PD), in particular for automatic peritoneal dialysis (APD).

2. Description of the Prior Art

Peritoneal dialysis is a treatment for purifying the blood of a patient affected by renal insufficiency. Unlike conventional haemodialysis, in peritoneal dialysis the membrane used to filter the blood does not consist of an artificial element provided outside the patient's body, but consists of the peritoneum. The peritoneum is a membrane situated in the abdomen and surrounding the internal organs. Since it is thin and highly vascularized it is possible to apply the physical principle of dialysis directly inside the patient's body.

Peritoneal dialysis requires a catheter which must be introduced permanently inside the abdomen so as to allow connection of the peritoneal cavity to an external circuit. The external circuit generally comprises a bag containing pure dialysate and a drainage outlet.

The treatment of peritoneal dialysis generally comprises a first infusion phase (or fill) during which the pure dialysate is supplied via the catheter to the peritoneal cavity. During the second so-called dwell phase, during which no external operations are required, dialytic exchange between the patient's blood and the dialysate takes place. During the third and final drainage stage (or drain) the saturated dialysate is removed from the peritoneal cavity.

In order to obtain satisfactory purification of the blood, the entire treatment cycle described above must be repeated several times in succession over the course of 24 hours. In the case of APD, the various treatment cycles are performed in succession throughout the night by means of a special machine called an "automatic cycler" which automatically sets and regulates the fill, dwell and drain phases.

In order to monitor the effectiveness and quality of the peritoneal dialysis treatment, it is known to analyse samples of saturated dialysate which is discharged.

For this reason, it has proved to be extremely useful to collect the samples of used dialysate at regular intervals and automatically, i.e. without the need for any intervention either by the patient or by other assisting persons. It is in fact desirable to eliminate any need for intervention, especially during the night, otherwise one of the main advantages of this treatment method is lost.

For these reasons there exists the need to introduce into the circuit a device which autonomously performs periodic sampling of dialysate samples.

A device of this type is described in WO 99/06082. This device, however, is not without drawbacks. It is, in fact, extremely complex since it is also intended to perform other functions, such as that of the cycler itself or also the preparation of the optimum dialysate solution for the individual patient.

SUMMARY OF THE INVENTION

The object of the present invention is therefore to overcome the drawbacks identified above in connection with the prior art.

In particular, a task of the present invention is to provide a device for collecting dialysate samples, having an extremely simple and robust structure and mode of operation.

Moreover, a task of the present invention is to provide a device for collecting dialysate samples, which does neither require external supply sources nor input control signals other than the flow rates.

The abovementioned object and tasks are achieved by a device for collecting dialysate samples having an inlet for receiving a flow of dialysate, a plurality of outlets for providing a flow of saturated dialysate, and means for sequentially selecting one of the outlets, with the sequential selection means being actuated only by the flow of dialysate received from the inlet.

BRIEF DESCRIPTION OF THE DRAWINGS

The characteristic features and the further advantages of the invention will emerge from the description, provided hereinbelow, of a number of examples of embodiment, provided purely by way of a non-limiting example, with reference to the accompanying drawings in which:

FIG. 10.*a* shows schematically a rotor of a device according to FIG. 6;

FIG. 10.*b* shows schematically a rotor of a device according to FIG. 8.

DETAILED DESCRIPTION OF THE PREFERRED EMBODIMENTS

Figure 1:
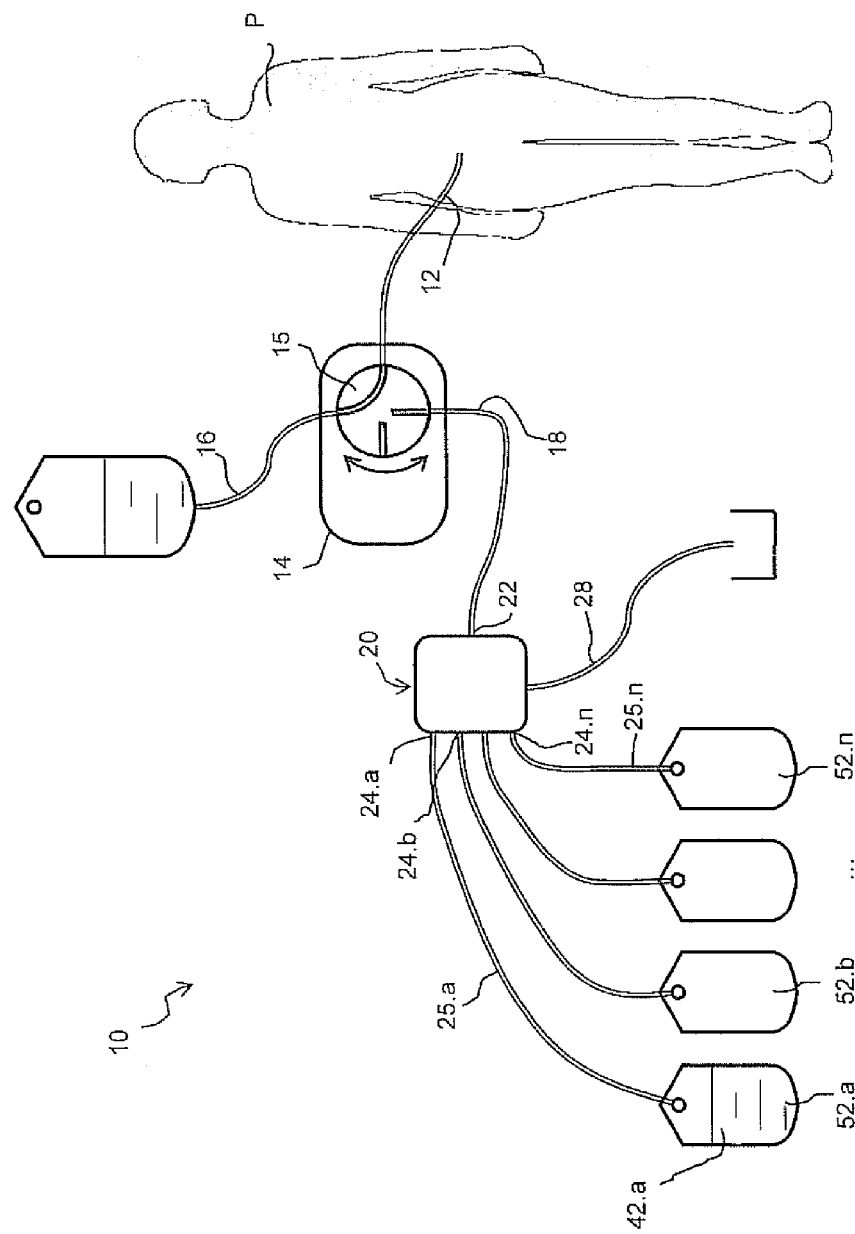
FIG. 1 shows schematically a circuit for peritoneal dialysis comprising a device for collecting samples according to the invention.

Further scope of applicability of the present invention will become apparent from detailed description given hereinafter. However, it should be understood that the detailed description and specific examples, while indicating preferred embodiments of the invention, are given by way of illustration only since various changes and modifications within the spirit and scope of the invention will become apparent to those skilled in the art from this detailed description.

The present invention relates to a device for collecting dialysate samples 42 denoted overall by 20. The device 20 comprises an inlet 22 for receiving a flow of dialysate, a plurality of outlets 24 for providing a flow of saturated dialysate and means 26 for sequential selection of one of the outlets 24. The sequential selection means 26 are activated only by the flow of dialysate received from the inlet 22.

In the description of the invention, reference will be made to the spatial arrangement of the device 20 which ensures correct operation thereof. During operation of the device 20, in fact, the force of gravity plays a decisive part, especially in the embodiments according to FIGS. 2 to 5. In particular, it will be assumed below that the force of gravity is directed as shown by the vector g in FIGS. 2 to 5 (side views).

With particular reference to the accompanying FIG. 1, a circuit 10 for peritoneal dialysis comprising a device 20 according to the invention is described. The circuit comprises a catheter 12 introduced into the patient P and designed to allow connection of the peritoneal cavity to the external circuit 10. The catheter 12 is connected to an automatic cycler 14 to which a line 16 supplying pure dialysate also leads. Finally, a drainage line 18 extends from the automatic cycler 14. The drainage line 18 forms the supply line of the device 20 according to the invention and is therefore connected to the inlet 22.

In FIG. 1, the automatic cycler 14 is shown schematically during the said fill phase, where the pure dialysate arriving from the supply line 16 is supplied to the catheter 12 and therefore to the peritoneal cavity of the patient P. The automatic cycler 14 is able, in a manner known per se, to manage also the other phases of the peritoneal dialysis treatment, i.e. the dwell phase and the drain phase. In the diagram according to FIG. 1, the various phases are managed by rotation of the selector 15. In particular, starting from the configuration shown in FIG. 1, an anti-clockwise rotation through 90° sets the circuit to the configuration for the dwell phase. Also, starting from the configuration shown in FIG. 1, a clockwise rotation through 90° (or an anti-clockwise rotation through 180° from the dwell configuration) sets the circuit to the configuration for the drain phase.

As can be seen in FIG. 1, the outlets 24 are designed to provide the flow of saturated dialysate for collection of a corresponding number of samples 42. For example samples 42 can be collected via tubes 25 in a corresponding number of repositories or bags 52. In the configuration shown in FIG. 1 there is an additional drainage line 28.

As already mentioned above, the sequential selection means 26 are activated only by the flow or by the temperature of saturated dialysate received from the inlet 22. In other words, the sequential selection means 26 do not require the supply of any external power, either for the operation of sensors or transducers which detect the status of the device 20, or for the operation of actuators or motor driven actuators which select the desired outlet 24 for the flow. The physical principles on which operation of the sequential selection means 26 are based represent the main differences between the various embodiments of the device 20 according to the invention.

Figure 2:
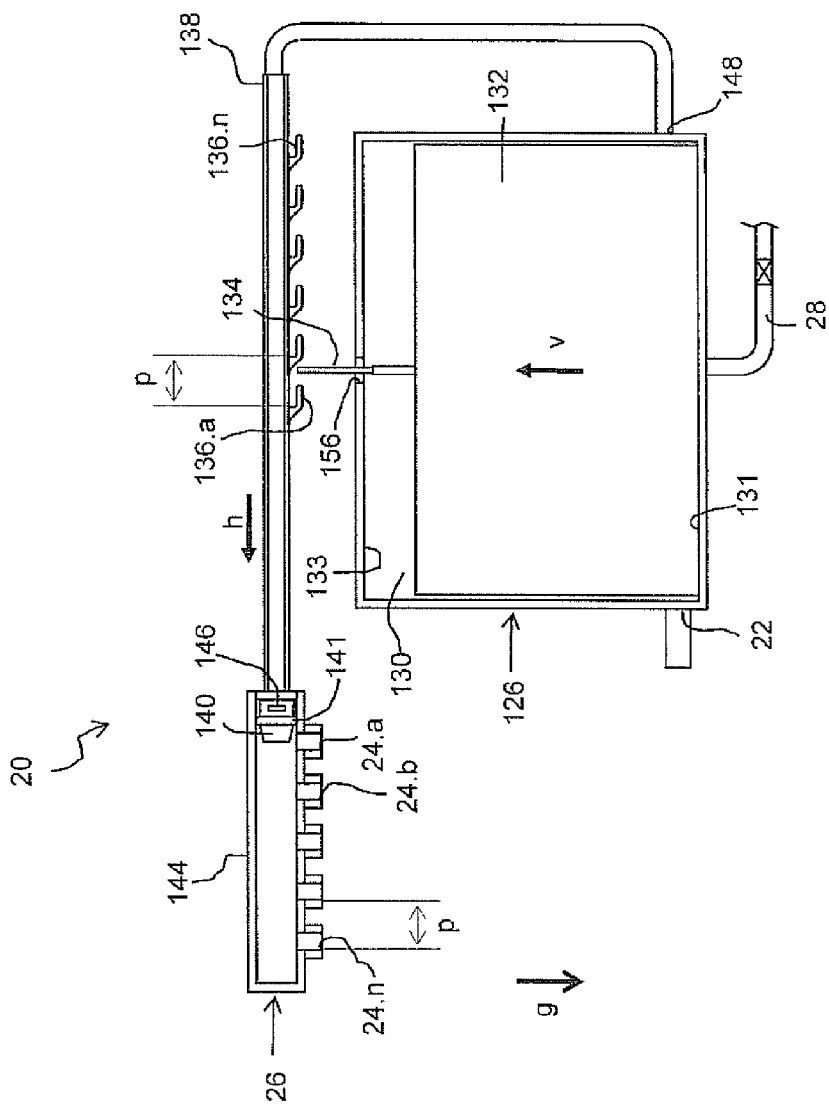
FIG. 2 shows schematically a first embodiment of the device for collecting samples according to the invention, in a first configuration.
Figure 3:
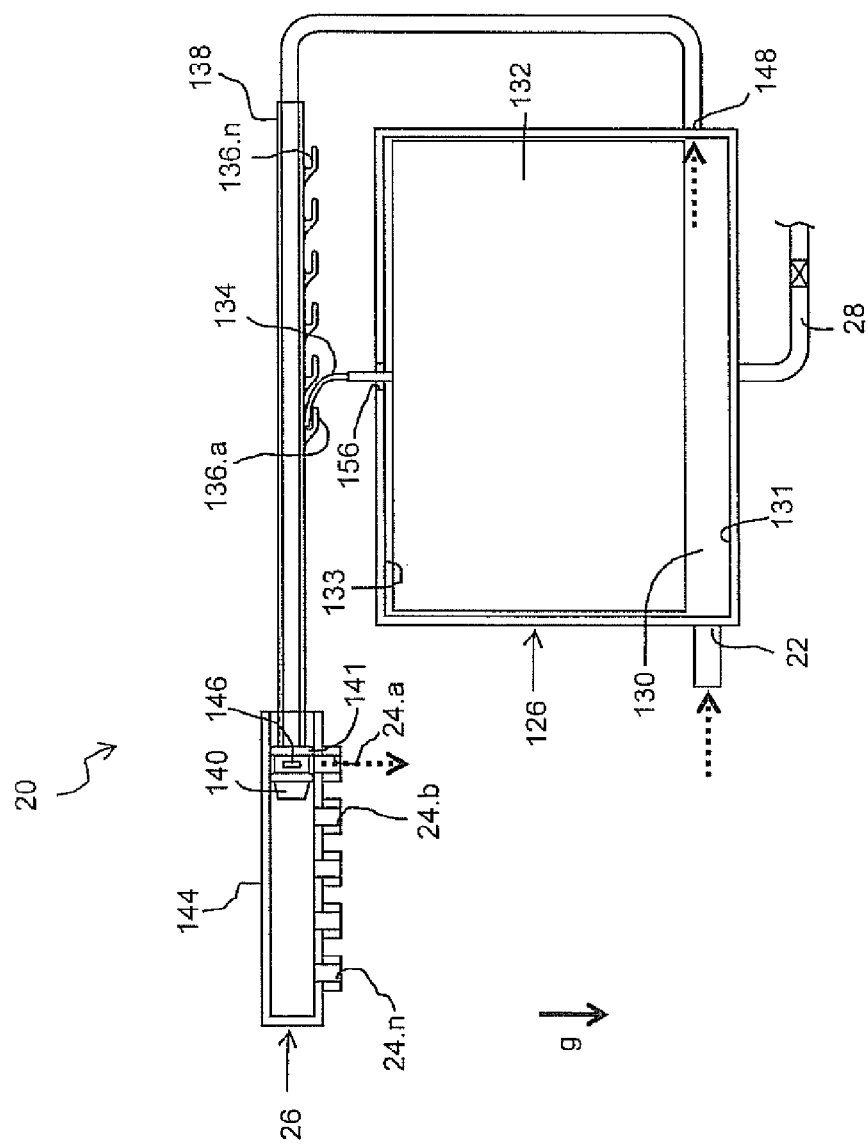
FIG. 3 shows the device according to FIG. 2 in a second configuration.
Figure 4:
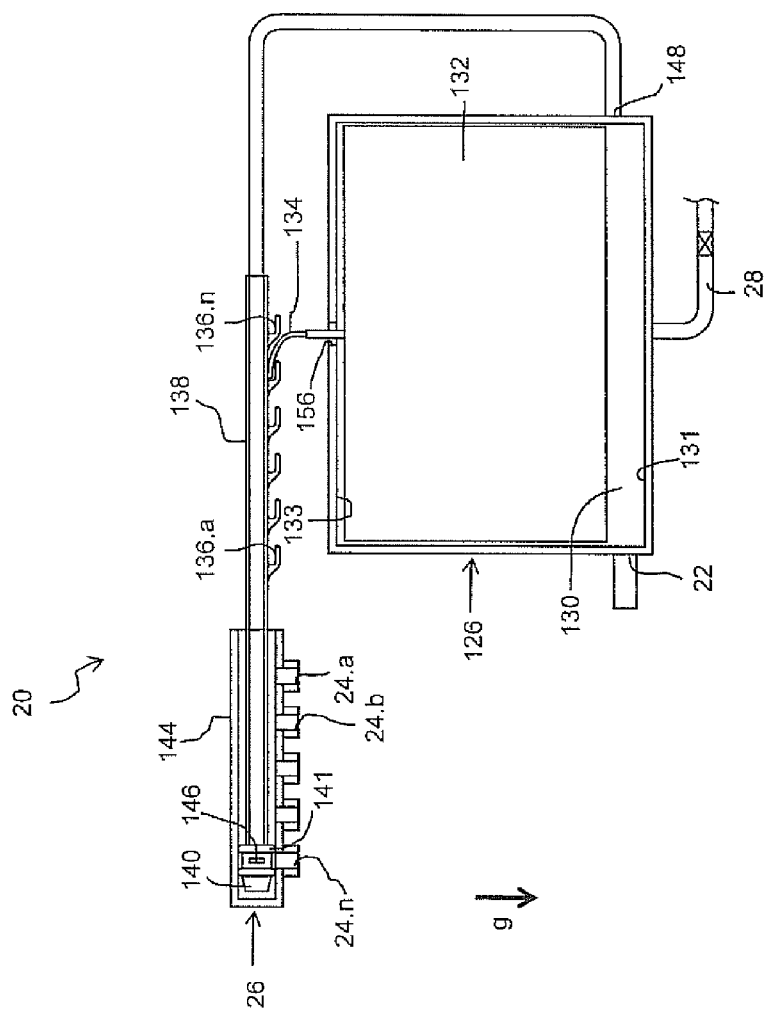
FIG. 4 shows the device according to FIG. 2 in a third configuration.

The embodiment of the device 20 shown schematically in FIGS. 2 to 4 is now described in detail. According to this embodiment, the device comprises a main chamber 130 housing a float 132 which occupies most of its volume. In particular, the float 132 is able to perform substantially only one movement: it is able to move vertically from a rest position substantially resting on the bottom 131 of the main chamber 130 into a working position substantially resting on the roof 133 of the main chamber 130. This movement is indicated by the arrow v in FIG. 1. The roof 133 of the main chamber 130 comprises preferably a vent 156.

A flexible actuator 134 is mounted on the float 132. The flexible actuator 134 is preferably mounted on the top surface of the float 132, perpendicularly with respect thereto. The flexible actuator 134 is designed to engage selectively with a single tooth of a plurality of teeth 136 integral with a hollow slider 138. The hollow slider 138 has a head 140 designed to slide inside a multiple connector 144 which defines the plurality of outlets 24. The pitch p which separates two successive teeth 136 on the hollow slider 138 is equal to the pitch p which separates two successive outlets 24 in the multiple connector 144. The head 140 comprises a radial opening 146 situated between two seals 141 for ensuring a seal against the inner walls of the multiple connector 144. Moreover, at the opposite end to the head 140, the hollow slider 138 is in fluid communication with the main chamber via an opening 148 formed in a wall of the latter in the vicinity of the bottom. In particular, the opening 148 is formed in a position such that it is covered by the float 132 when the latter is at the bottom end of its travel path and is uncovered when the float 132 is at the top end of its travel path. The volume of the float 132 is designed in order to overcome the friction resistance generated by head 140 during its movement along the multiple connector 144.

Finally, the device 20 comprises a drainage line 28 which extends from the bottom 131 of the main chamber 130. The drainage line 28 may comprise a valve for regulating and/or interrupting the flow or may comprise, preferably, a narrowing for slowing down significantly the flow inside it.

Operation of the device 20 according to the embodiment shown in FIGS. 2 to 4 is now described. When the automatic cycler 14 activates the start of the drain phase, the saturated dialysate leaving the catheter 12 flows along the drainage line 18 and reaches the inlet 22 of the device 20. The flow of the saturated dialysate reaches the main chamber 130. The configuration of the device 20 ensures that the incoming mass of dialysate is positively balanced. The drainage line 28, in fact, is completely closed (in the embodiments comprising a valve) or is greatly narrowed. It is thus ensured that any outgoing flow along the drainage line 28 is significantly less than the incoming flow through the inlet 22. This ensures that the volume of saturated dialysate inside the main chamber 130 increases continuously, generating a floating thrust on the float 132. The floating thrust raises the float from the rest position (see arrow v in FIG. 1) towards the working position. The upward movement of the float 132 has two separate effects. A first effect is that of freeing the opening 148, allowing the dialysate to access it. The other effect is that the floating force is transmitted to the flexible actuator 134 which is formed so as to engage with the first tooth 136.*a*, adapting its form thereto. The flexible actuator 134 then converts the vertical movement of the float 132 (arrow v) into a horizontal movement of the hollow slider 138 (arrow h). The horizontal movement of the hollow slider 138 produces the forward movement of the head 140 over a distance p inside the multiple connector 144. The head 140 thus isolates the first outlet 24.*a* between the two seals 141 and substantially aligns the radial opening 146 with it. FIG. 3 shows the configuration thus assumed by the device 20. It can be noted, in fact, how the movement of the float 132 has, on the one hand, freed the opening 148 and, on the other hand, aligned the radial opening 146 with the outlet 24.*a*. It can therefore be noted how a fluid path has been established (see dotted arrows in FIG. 3) such that the saturated dialysate is able to flow freely from the inlet 22 to the first outlet 24.*a* and then be collected as a first sample 42.*a* inside the repository or bag 52.*a* (see FIG. 1).

According to some embodiments, each bag 52 is able to contain the entire volume of saturated dialysate expelled during the entire drain phase. In such a case a small quantity of dialysate (for example 1%) to be used as a sample will be subsequently removed from the entire volume, probably the next day in the clinic. According to other embodiments, each bag 52 is instead able to contain only a small quantity of dialysate to be used as a sample, while all the remaining volume is drained in a manner known per se.

At the end of the drain phase, the flow of saturated dialysate to the inlet 22 is interrupted. Both in the case where the drainage line 28 comprises a valve and in the case where it is only greatly narrowed, the volume of dialysate inside the main chamber 130 starts to diminish. In the first case, in fact, the valve during this phase is open, allowing the flow along the drainage line 28. In the second case, however, the outlet flow, although minimal, is not balanced by any incoming flow. The volume of saturated dialysate inside the main chamber 130 diminishes, reducing the floating thrust on the float 132 which gradually moves downwards from the working position into the rest position. The downwards movement of the float 132 causes the opening 148 to be covered again and disengages the flexible actuator 134 from the first tooth 136.*a*. As will be clear to a person skilled in the art, the flexible actuator 134 and the teeth 136 are formed so as not to transmit any movement to the hollow slider 138 during the downward movement of the float 132. The head 140 of the hollow slider 138 therefore maintains the position assumed previously inside the multiple connector 144. The configuration thus assumed by the device 20 is partially shown in the FIG. 2 (position of the float 132 only) and partially shown in FIG. 3 (position of the hollow slider 138 only). At this point the device 20 is ready for the next operating cycle which, in a manner entirely similar to that described above, will cause displacement of the hollow slider 138 over a further distance p so as to bring the head 140 opposite the second outlet 24.*b*. A second sample 42.*b* is thus collected inside the second bag 52.*b* (see FIG. 1).

This operating cycle may be repeated any number of times required until, at the end of the APD treatment, the last outlet 24.*n* is reached (as shown in FIG. 4).

The figures show a multiple connector 144 with five outlets, but it is obvious that, in order to satisfy specific requirements, it is possible to provide a different number of outlets without any substantial modification of the device 20.

Figure 5:
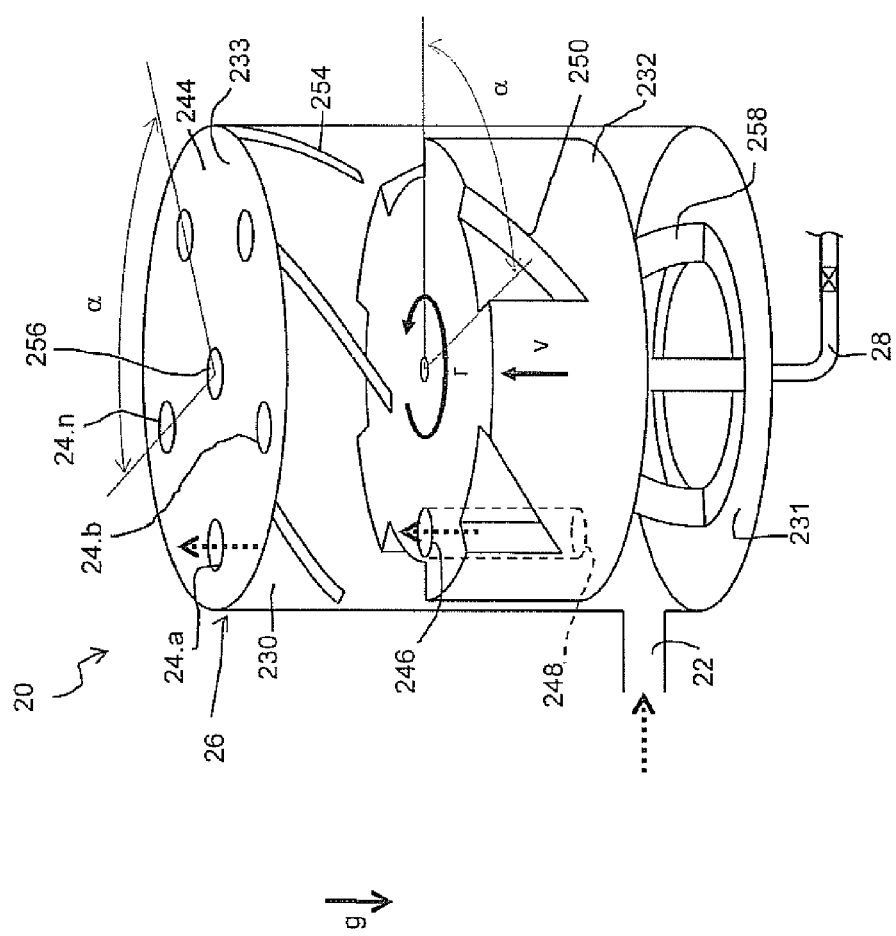
FIG. 5 shows schematically a second embodiment of the device for collecting samples according to the invention.

The embodiment of the device 20 shown schematically in FIG. 5 is now described in detail below. According to this embodiment, the device comprises a main chamber 230 housing a float 232 which occupies most of its volume. Both the main chamber 230 and the float 232 have a substantially cylindrical shape. The float 232 is able to perform two movements: a first vertical translatory movement from a rest position substantially resting on the bottom 231 of the main chamber 230 into a working position substantially resting on the roof 233 of the main chamber 230; a second rotational movement about its vertical axis. These movements are indicated by the arrow v and by the arrow r in FIG. 5, respectively.

Helical grooves 250 are formed in the float 232 and are designed to engage with corresponding shaped threads 250 formed inside the main chamber 230. A duct is formed inside the float 232 and connects an opening 248 in the bottom of the float to another opening 246 fainted at the top.

The roof 233 of the main chamber 230 performs the function of a multiple connector 244 and defines the plurality of outlets 24. The outlets 24 are situated at the same radial distance from the axis of the main chamber 230 and are circumferentially spaced in an equidistant manner. The angle α which separates two successive outlets 24 on the roof 230 is equal to the angle α of extension of the shaped threads 254. It should be noted that FIG. 5 is not precise in this respect. The roof 233 of the main chamber 230 also comprises a vent 256 which is preferably protected by a semi-permeable membrane.

The bottom 231 of the main chamber comprises centring means 258 designed to cooperate with the bottom of the float 232.

Finally, the device 20 comprises a drainage line 28 which extends from the bottom 231 of the main chamber 230. The drainage line 28 may comprise a valve for regulating and/or interrupting the flow or may comprise, preferably, a narrowing for slowing down significantly the flow inside it.

Operation of the device 20 according to the embodiment shown in FIG. 5 is now described. When the automatic cycler 14 activates the start of the drain phase, the saturated dialysate leaving the catheter 12 flows along the drainage line 18 and reaches the inlet 22 of the device 20. The flow of saturated dialysate reaches the main chamber 230. The configuration of the device 20 ensures that the incoming mass of dialysate is positively balanced. In fact, in its preferred embodiment, the drainage line 28 is always open and greatly narrowed. In an alternative embodiment the drainage line 28 comprises a valve which can completely close or greatly narrow it. It is thus ensured that any outgoing flow along the drainage line 28 is significantly less than the incoming flow through the inlet 22. This ensures that the volume of saturated dialysate inside the main chamber 230 increases continuously, generating a floating thrust on the float 232. The floating thrust raises the float from the rest position (see arrow v in FIG. 5) towards the working position. The upward movement of the float 232 has the other effect of causing the helical grooves 250 to engage with the shaped threads 254. The vertical movement of the float 232 (arrow v) therefore generates a rotary movement thereof (arrow r). The rotary movement of the float 232 causes alignment of the opening 246 with the first outlet 24.*a*. A fluid path is thus established (see dotted arrows in FIG. 5) such that the saturated dialysate is able to flow freely from the inlet 22 to the first outlet 24.*a* and then be collected as a first sample 42.*a* inside the bag 52.*a* (see FIG. 1).

At the end of the drain phase, the flow of saturated dialysate to the inlet 22 is interrupted. Both in the case where the drainage line 28 comprises a valve and in the case where it is only greatly narrowed, the volume of dialysate inside the main chamber 230 starts to diminish. In the first case, in fact, the valve during this phase is open, allowing the flow along the drainage line 28. In the second case, however, the outlet flow, although minimal, is not balanced by any incoming flow. The volume of saturated dialysate inside the main chamber 230 diminishes, reducing the floating thrust on the float 232 which gradually moves downwards from the working position into the rest position. As will be clear to a person skilled in the art, the helical grooves 250 and the shaped threads 254 are formed so as not to produce any movement of the float 132 during its downward movement. The opening 246 therefore maintains the angular position assumed previously.

At this point the device 20 is ready for the next operating cycle which, in a manner entirely similar to that described above, will cause rotation of the float 132 through a further angle α so as to bring the opening 246 opposite the second outlet 24.*b*. A second sample 42.*b* is thus collected inside the second bag 52.*b* (see FIG. 1).

This operating cycle may be repeated any number of times required until, at the end of the APD treatment, the last outlet 24.*n* is reached.

FIG. 5 shows a multiple connector 244 with five outlets, but it is obvious that, in order to satisfy specific requirements, it is possible to provide a different number of outlets without any substantial modification of the device 20.

Figure 6:
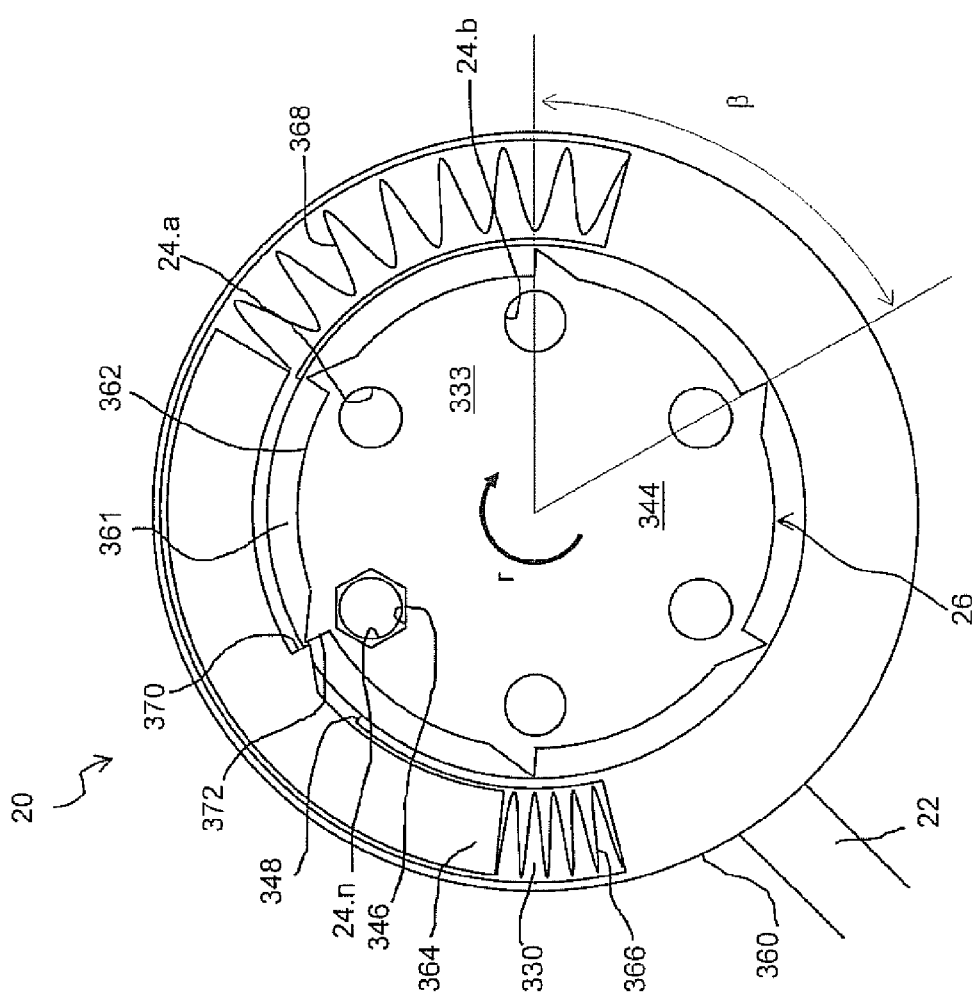
FIG. 6 shows schematically a plan view of a third embodiment of the device for collecting samples according to the invention, in a first configuration.
Figure 7:
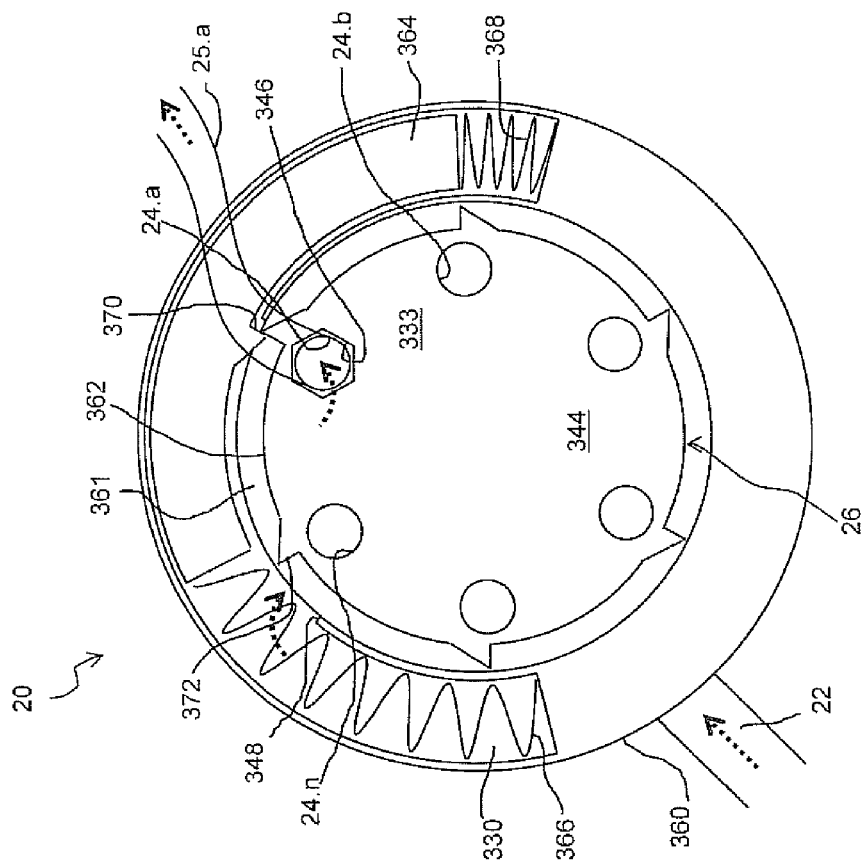
FIG. 7 shows the device according to FIG. 6 in a second configuration.

The embodiment of the device 20 shown schematically in FIGS. 6 and 7 is now described in detail. According to this embodiment, the device comprises a stator 360 and a rotor 362 housed in a central chamber 361 inside the stator 360. An annular chamber 330 accessed by the inlet 22 is formed around the central chamber 361. A curved slider 364, which is acted on by two oppositely directed thrusts, is housed inside the central chamber 361. A first thrust is provided by a thruster 366 made of a shape memory material, such as a shape memory alloy (SMA) or a shape memory polymer (SMP). A well-known shape memory material is the nickel and titanium based alloy called Nitinol. The thruster 366 tends to cause rotation of the curved slider 364 in one direction inside the annular chamber 330. A second thrust is provided by a spring 368 of the conventional type and tends to cause rotation of the curved slider 364 in the opposite direction inside the annular chamber 330. In accordance with the example shown schematically in FIGS. 6 and 7, the thruster 366 tends to cause rotation of the curved slider 364 in a clockwise direction, while the spring 368 tends to cause it to rotate in an anti-clockwise direction. The equilibrium condition of the curved slider 364 is reached, in a manner known per se, when the two thrusts are equal.

The shape memory alloy (SMA) which forms the thruster 366 is able, in a manner known per se, to modify its structure when there is a variation in temperature. In this specific case, the SMA is able to pass from a martensitic structure, which is stable at temperatures less than 34° C., to an austenitic structure, which is stable at temperatures higher than 34° C. The change in the internal structure of the alloy results in a corresponding change in shape of the thruster 366. In particular, FIG. 6 shows the device 20 in a condition where the internal temperature is stably less than 34° C. In this condition, the thruster 366 is in its more compressed configuration and therefore the curved slider 364 is pushed by the spring 368 to the anti-clockwise end of its angular travel path. Vice versa, FIG. 7 shows the device 20 in a condition where the internal temperature is stably higher than 34° C. In this condition, the thruster 366 is in its more expanded configuration and therefore the curved slider 364 is pushed against the spring 368 at the clockwise end of its angular travel path. The entire angular travel path of the curved slider 364 covers an angle β.

The annular chamber 330 is in fluid communication with the central chamber 361 via a passage 348. In particular, the passage 348 is formed in a position such that it is covered by the curved slider 364 when the latter is at the anti-clockwise end of its travel path and is uncovered when the curved slider 364 is at the clockwise end of its travel path.

The curved slider 364 is provided with first engaging means 370 designed to engage with corresponding second engaging means 372 provided on the rotor. The engaging means 370 and 372 are formed so as to allow engagement in one sense only, in the example in question in the clockwise direction.

The roof 333 of the main chamber 361 of the stator 360 performs the function of a multiple connector 344 and defines the plurality of outlets 24. Each outlet 24 of the device 20 is connected to a tube 25 in facts. In FIGS. 6 and 7, most tubes 25 have been removed for sake of clarity. Only one tube 25 appears in FIG. 7, connected to the open outlet 24.a. The outlets 24 are situated at the same radial distance from the axis of the stator 360 and are circumferentially spaced in an equidistant manner. The angle β which separates two successive outlets 24 on the roof 230 is equal to the angle β traveled by the curved slider 364.

Figure 9:
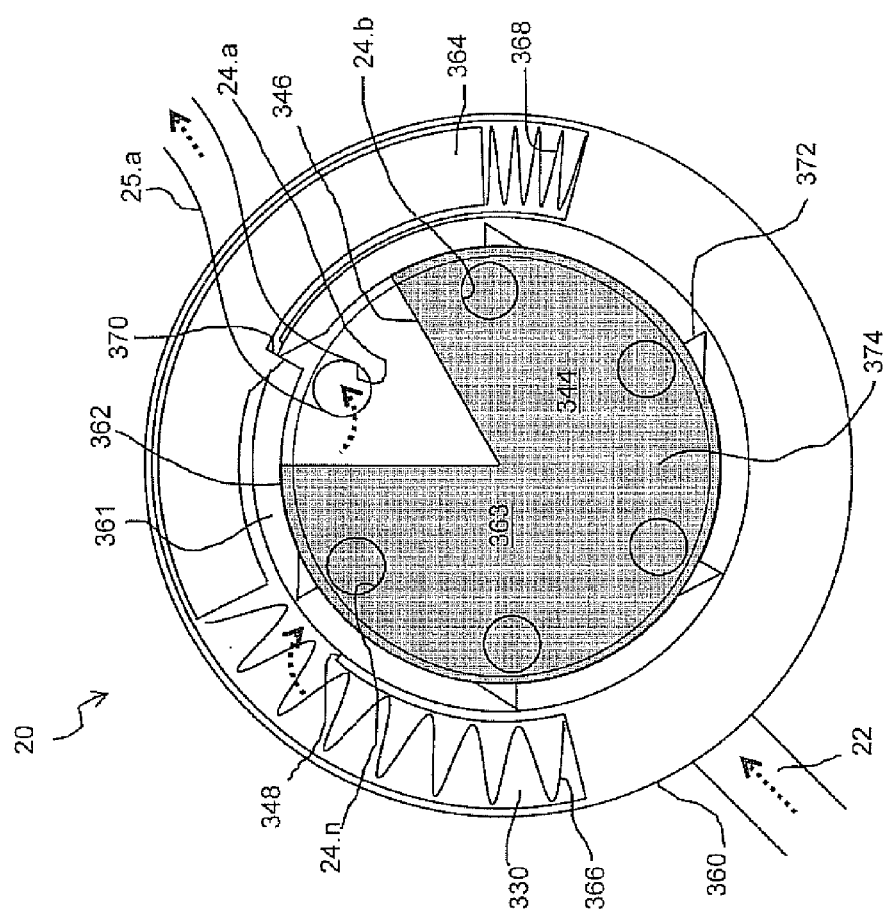
FIG. 9 shows the device according to FIG. 8 in a second configuration.

The rotor 362 comprises an opening 346 on its top wall 363 (see also FIG. 9.a). The top wall 363 is able to obstruct every outlet 24 but the one in line with the opening 346. The opening 346, according to FIGS. 6, 7 and 9.a, has a hexagonal shape just to be easily distinguished from the outlets 24. Of course any other shape can be used for the opening 346.

Operation of the device 20 according to the embodiment shown in FIGS. 6 to 7 is now described. When the automatic cycler 14 activates the start of the drain phase, the saturated dialysate leaving the catheter 12 flows along the drainage line 18, reaches the inlet 22 of the device 20 and accesses the annular chamber 330. This results in an increase of the temperature inside the annular chamber 330 from the ambient temperature (typically less than 34° C.) to the body temperature of the patient P (greater than 34° C.). This thus produces the change in the structure of the SMA and therefore the change in shape of the thruster 366. The thrust in the clockwise direction imparted to the curved slider 364 thus overcomes the thrust of the spring 368, therefore moving the curved slider 364 to the clockwise end of its angular travel path. In other words, the change in shape of the thruster 366 moves the curved slider 364 from the position shown in FIG. 6 to the position shown in FIG. 7. During rotation of the curved slider 364, the rotor 362 is also moved as a result of the engaging means 370 and 372. The rotational movement of the rotor 362 causes the opening 346 to be aligned with the first outlet 24.a. A fluid path is thus established (see dotted arrows in FIG. 7) such that the saturated dialysate is able to flow freely from the inlet 22, through the first outlet 24.a, along the tube 25.a and then be collected as a first sample 42.a inside the bag 52.a (see FIG. 1). At the end of the drain phase, the flow of saturated dialysate to the inlet 22 is interrupted and the remaining dialysate in the device 20 flows completely into the selected sample bag 52.a. The temperature inside the annular chamber 330 then decreases from the body temperature of the patient P (greater than 34° C.) and reaches again the ambient temperature (typically less than 34° C.). This thus produces a new change in the structure of the SMA and therefore a new change in shape of the thruster 366. The thrust in the anti-clockwise direction imparted to the curved slider 364 by the spring 368 thus moves the curved slider 364 back to the anti-clockwise end of its angular travel path. In other words, the change in shape of the thruster 366 moves the curved slider 364 from the position shown in FIG. 7 back into the position shown in FIG. 6. The anti-clockwise rotation of the curved slider 364 does not cause the movement of the rotor 362 owing to the particular form of the engaging means 370 and 372. The opening 346 therefore maintains the angular position assumed previously.

At this point the device 20 is ready for the next operating cycle which, in a manner entirely similar to that described above, will cause renewed rotation of the curved slider 364 so as to impart a further rotation of the rotor 362 through a further angle β and thus bring the opening 346 opposite the second outlet 24.b. A second sample 42.b is thus collected inside the second bag 52.b (see FIG. 1).

This operating cycle may be repeated any number of times required until, at the end of the APD treatment, the last outlet 24.n is reached.

Figure 8:
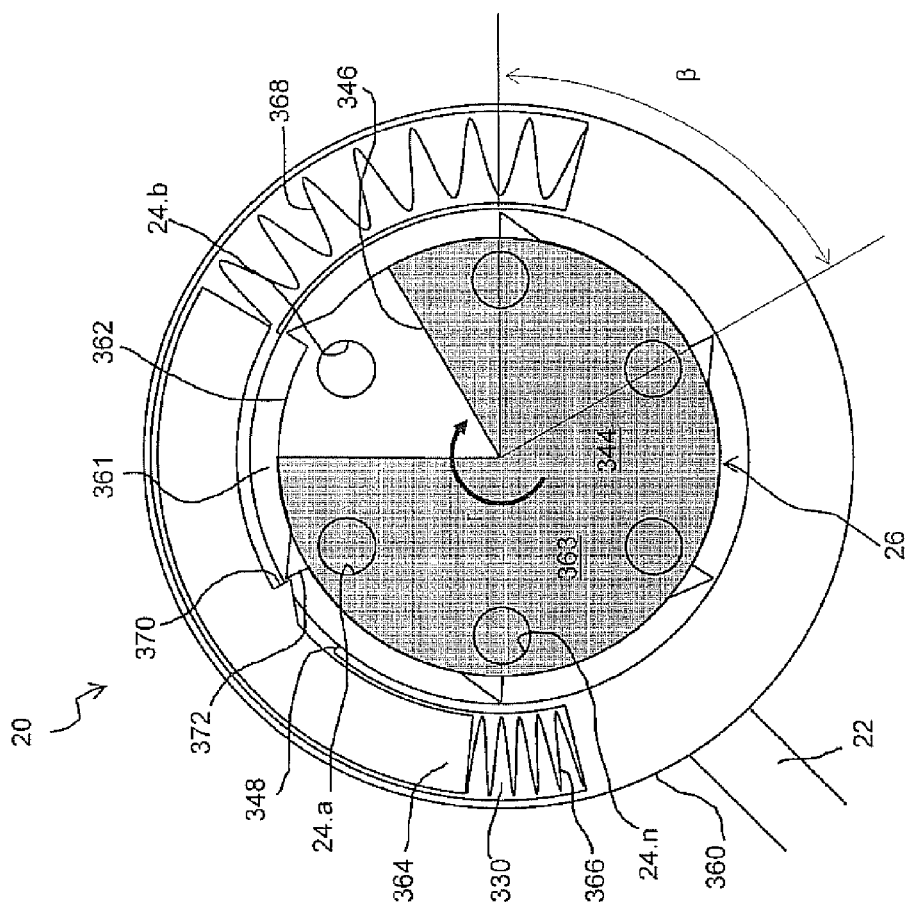
FIG. 8 shows schematically a plan view of a fourth embodiment of the device for collecting samples according to the invention, in a first configuration.

The embodiment of the device 20 shown schematically in FIGS. 8 and 9 is now described in detail. This embodiment is very similar to the one described above with reference to FIGS. 6 and 7. Thus, only the differences will be described in the following, while for the similar parts reference is made to the previous description. Same elements are identified with same reference numbers. The device 20 comprises a stator 360 and a rotor 362. The top wall 363 of the rotor 362 performs the function of a multiple connector 344 and defines the plurality of outlets 24. Each outlet 24 of the device 20 is connected to a tube 25 in facts (see also FIG. 10.*b*). In FIGS. 8 and 9, most tubes 25 have been removed for sake of clarity. Only one tube 25 appears in FIG. 9, connected to the open outlet 24.*a*. The outlets 24 are situated at the same radial distance from the axis of the rotor 362 and are circumferentially spaced in an equidistant manner. The angle β which separates two successive outlets 24 on the rotor 362 is equal to the angle β traveled by the curved slider 364. The stator 360 comprises a wall 374 defining an opening 346. The wall 374 is able to obstruct every outlet 24 but the one in line with the opening 346. According to FIGS. 8 and 9, the opening 346 has a circular-sector shape just to be easily distinguished from the outlets 24. Of course any other shape can be used for the opening 346.

Operation of the device 20 according to the embodiment shown in FIGS. 8 and 9 is now briefly described. When the dialysate accesses the annular chamber 330, the thruster 366 changes its shape. The thrust moves the curved slider 364 to the clockwise end of its angular travel path, uncovering the passage 348. During rotation of the curved slider 364, the rotor 362 is also moved as a result of the engaging means 370 and 372. The rotational movement of the rotor 362 causes the first outlet 24.*a* to be aligned with the opening 346 of the stator 360. A fluid path is thus established (see dotted arrows in FIG. 9) such that the saturated dialysate is able to flow freely to the bag 52.*a*.

When the flow of saturated dialysate is interrupted, the remaining dialysate flows completely from the device 20 into the sample bag 52.*a*. The temperature inside the annular chamber 330 decreases producing a new change in the shape of the thruster 366 which 366 moves back the curved slider 364. The anti-clockwise rotation of the curved slider 364 does not cause the movement of the rotor 362 and the outlets 24 maintain the angular position assumed previously.

The device 20 is ready for the next operating cycle. A new rotation of the curved slider 364 will impart a further rotation of the rotor 362 through a further angle β bringing the second outlet 24.*b* in line with the opening 346.

This operating cycle may be repeated any number of times required until, at the end of the APD treatment, the last outlet 24.*n* is reached.

The difference between the two above described embodiments, the one shown in FIGS. 6 and 7 and the one shown in FIGS. 8 and 9, can be easily appreciated considering the shape and function of the respective rotors, shown in FIGS. 10.*a* and 10.*b*. As can be seen in FIG. 10.*a*, the rotor 362 of the embodiment shown in FIGS. 6 and 7 has one opening 346 only. Such opening 346 is intended to rotate so as to successively enable one of the outlets 24 provided on the stator 360. On the contrary, as can be seen in FIG. 10.*b*, the rotor 362 of the embodiment shown in FIGS. 8 and 9 has a plurality of outlets 24. Such outlets 24 are intended to rotate so as to be successively enabled by the only opening 346 provided on the stator 360.

FIGS. 6 to 9 show multiple connectors 344 with six outlets, but it is obvious that, in order to satisfy specific requirements, it is possible to provide a different number of outlets without any substantial modification of the device 20.

With reference to the embodiments of the device for collecting dialysate samples described above, the person skilled in the art may, in order to satisfy specific requirements, make modifications to and/or replace elements described with equivalent elements, without thereby departing from the scope of the accompanying claims.

What is claimed is:

1. A device for collecting dialysate samples, comprising:
   an inlet for receiving a flow of dialysate;
   a plurality of outlets for providing a flow of saturated dialysate; and
   a sequential selection element for sequentially selecting one of said plurality of outlets,
   the sequential selection element being actuated only by the flow of dialysate received from the inlet.

2. The device according to claim 1, wherein said plurality of outlets is defined by a multiple connector.

3. The device according to claim 2, wherein said sequential selection element includes a float suitable to generate a floating thrust when reached by said flow of dialysate.

4. The device according to claim 3, wherein said float is able to move vertically from a rest position to a working position, so as to act on a hollow slider designed to slide inside said multiple connector.

5. The device according to claim 4, wherein said hollow slider includes a radial opening adapted to be selectively aligned with any of said outlets.

6. The device according to claim 3, wherein said float is able to move vertically from a rest position to a working position and to rotate about a vertical axis thereof, with respect to said multiple connector.

7. The device according to claim 6, wherein said float includes a duct connecting an opening in a bottom of the float to another opening formed at a top of the float, the opening being adapted to be selectively aligned with any of said outlets.

8. The device according to claim 1, wherein said sequential selection element includes a thruster made of a shape memory material and suitable to change a shape thereof when reached by said flow of dialysate.

9. The device according to claim 8, wherein said thruster is suitable to act on a rotor that includes an opening, the opening being adapted to be selectively aligned with any of said outlets.

10. The device according to claim 1, further comprising a drainage line.

11. A system for peritoneal dialysis comprising a device according to claim 1, said system having a tubeset comprising:
    a supply line for connection to, or being connected to, the inlet of the device and
    at least one repository for connection to, or being connected to, one of the outlets of the device.

12. The system according to claim 11, further comprising a drainage line connected to the device.

13. A device for collecting dialysate samples, comprising:
    an inlet for receiving a flow of dialysate;
    a plurality of outlets for providing a flow of saturated dialysate; and
    a sequential selection element for sequentially selecting one of said plurality of outlets, the sequential selection element (i) being actuated by the flow of dialysate received from the inlet and (ii) having a transmittable thrust element that generates a transmittable thrust when contacted by said flow of dialysate.

14. The device according to claim 13, wherein the plurality of outlets is configured as a multiple connector.

15. The device according to claim 14, wherein the transmittable thrust element is a float.

16. The device according to claim 15, wherein the float is configured (i) to move vertically from a rest position to a working position and (ii) to act on a hollow slider that slides inside the multiple connector.

17. The device according to claim 13, wherein the transmittable thrust element acts on a rotor having an opening that is configured to be selectively aligned with any of the plurality of outlets.

18. The device according to claim 13, wherein the transmittable thrust element (i) has a material of construction that is a shape memory material and (ii) is configured to change in shape when impacted by the flow of dialysate.

* * * * *

UNITED STATES PATENT AND TRADEMARK OFFICE
CERTIFICATE OF CORRECTION

PATENT NO. : 9,072,835 B2  
APPLICATION NO. : 13/322993  
DATED : July 7, 2015  
INVENTOR(S) : Veneroni et al.

It is certified that error appears in the above-identified patent and that said Letters Patent is hereby corrected as shown below:

Title Page, Item (73) in the Assignee:

Change "Presenius Medical Care Deutschland Gmbh" to --Fresenius Medical Care Deutschland GmbH--.

Signed and Sealed this  
Twenty-sixth Day of January, 2016

Michelle K. Lee  
*Director of the United States Patent and Trademark Office*